United States Patent
Gansemer et al.

(10) Patent No.: US 7,086,274 B2
(45) Date of Patent: Aug. 8, 2006

(54) METHOD AND APPARATUS FOR MEASURING GAS CONCENTRATION LEVELS IN LIQUIDS

(75) Inventors: Todd M. Gansemer, Eldridge, IA (US); Jim N. Hart, Davenport, IA (US)

(73) Assignee: Alcoa Inc., Pittsburgh, PA (US)

( * ) Notice: Subject to any disclaimer, the term of this patent is extended or adjusted under 35 U.S.C. 154(b) by 202 days.

(21) Appl. No.: 10/738,820

(22) Filed: Dec. 17, 2003

(65) Prior Publication Data

US 2005/0132776 A1    Jun. 23, 2005

(51) Int. Cl.
*G01N 33/20* (2006.01)
(52) U.S. Cl. .................... 73/19.1; 73/19.07
(58) Field of Classification Search .............. 73/19.07, 73/19.1
See application file for complete search history.

(56) References Cited

U.S. PATENT DOCUMENTS

| | | |
|---|---|---|
| 2,861,450 A | 11/1958 | Ransley |
| 3,451,256 A | 6/1969 | Kolodney |
| 4,257,257 A | 3/1981 | Dairaku et al. |
| 4,261,330 A * | 4/1981 | Reinisch ............... 126/705 |
| 4,454,748 A | 6/1984 | Terai et al. |
| 4,757,707 A | 7/1988 | Harvey et al. |
| 4,907,440 A | 3/1990 | Martin et al. |
| 4,998,432 A * | 3/1991 | Plessers et al. ............ 73/19.07 |
| 5,031,444 A | 7/1991 | Doutre et al. |
| 5,591,894 A * | 1/1997 | Falk et al. ................. 73/19.07 |
| 6,216,526 B1 * | 4/2001 | Junker et al. .............. 73/19.07 |
| 6,277,329 B1 * | 8/2001 | Evans ........................ 422/80 |
| 2004/0190571 A1 * | 9/2004 | Sutton et al. ................ 372/36 |

OTHER PUBLICATIONS

"Analyzer for hydrogen in liquid aluminum", ABB Inc., pp. 1-4, CANADA.
Martin et al., "Alscan: A New and Simple Technique for In-Line Analysis of Hydrogen in Aluminium Alloys", Light Metals 1989, pp. 903-912, CANADA.
Dupuis et al., "An Analysis of Factors Affecting the Response of Hydrogen Determination Techniques for Aluminum Alloys", Light Metals 1992—The Minerals, Metals & Materials Society, 1991, pp. 1055-1067, CANADA.
Ray, "A Comparative Assessment of Quantitative Hydrogen Analyzers Commonly Used in the Aluminum Industry", Light Metals 1992—The Minerals, Metals & Materials Society, 1991, pp. 1031-1047, Richmond, Virginia.
Ray, "Long-Term Assessment of the Alscan Hydrogen Analyzer", pp. 1-6, Richmond, Virginia.

* cited by examiner

*Primary Examiner*—Hezron Williams
*Assistant Examiner*—Paul M. West
(74) *Attorney, Agent, or Firm*—Greenberg Traurig LLP; Harry A. Hild, Jr.

(57) ABSTRACT

A method and apparatus for measuring the concentration of gas, such as hydrogen, in a liquid, such as molten aluminum, without requiring a bias or adjustment to compensate for variations in ambient conditions, such as humidity. A measurement system includes a probe connected to an analyzer with a housing enclosing a pump assembly. The measurement system may include a climate-controlled environment substantially devoid of ambient humidity and surrounding at least the pump assembly. A modified pump assembly includes at least one seal, at least one diaphragm and at least one gasket made from a material compatible with hydrogen and substantially unaffected by ambient humidity. A method of use is also disclosed.

17 Claims, 7 Drawing Sheets

METHOD AND APPARATUS FOR MEASURING GAS CONCENTRATION LEVELS IN LIQUIDS

BACKGROUND OF THE INVENTION

1. Field of the Invention

The present invention relates generally to a method for measuring the concentration of a gas in a liquid and, more particularly, to a method of measuring the hydrogen content in molten aluminum and alloys thereof, without having to undesirably compensate for variations in ambient conditions, such as, for example, humidity. The invention also relates to apparatus for facilitating such measurement.

2. Background Information

Hydrogen gas is frequently formed upon exposure of a molten metal, such as molten aluminum, to moisture, such as atmospheric humidity. Hydrogen is much more soluble in molten aluminum and its alloys than in solid state aluminum. Therefore, when molten aluminum starts to solidify, hydrogen solubility rapidly decreases forcing the expulsion of the extraneous gas content. This phenomenon is commonly known in the art as out-gassing. Out-gassing is responsible for metallurgical problems, such as, for example, blisters, voids, blow holes, and reduced corrosion resistance. Accordingly, minimizing such problems requires accurate knowledge of the hydrogen gas content in the molten metal.

There are several known techniques for testing, or extracting hydrogen from, prepared solid aluminum samples, for example, in a laboratory remote from the aluminum casting shop or foundry. One such quantitative laboratory analysis technique is commonly known in the art as Hot Vacuum Subfusion Extraction, also known as the Ransley Method. However, it is well known in the art that analysis of molten aluminum hydrogen concentration levels through "on-line" measuring, or measuring during the aluminum casting process, provides the easiest, fastest, most reproducible and most suitable, on-cite measurement method for aluminum casting shops and foundries.

Known methods and apparatus for determining hydrogen concentrations in molten aluminum typically employ a measurement probe, immersed in the molten metal, and an analyzer for analyzing measurements taken by the probe and for providing a readout of the hydrogen concentration. See, e.g., U.S. Pat. Nos. 2,861,450 and 4,907,440, which are hereby incorporated herein by reference. Three such systems are commonly known in the industry under the names TELEGAS, developed by Alcoa, Incorporated of Alcoa Center, Pennsylvania, ALSCAN, developed by ABB Incorporated of Quebec, Canada and NOTORP, developed by TYK Refractories Company, of Clairton, Penn.

FIG. 1 illustrates a measurement system 2, such as the ALSCAN system manufactured by ABB Incorporated of 585 Charest Boulevard, East, Suite 300, Quebec, Canada. As shown, the measurement system 2 may be directly attached to a launder 16 in, for example, an aluminum casting shop. The measurement system 2 includes a probe 4 structured to be immersed into the molten aluminum 18 and an analyzer 6 for processing data retrieved by the probe 4. See, e.g., U.S. Pat. No. 4,907,440. As shown, the housing 8 of the analyzer 6 encloses a gas reservoir 10 containing an inert reference or carrier gas, such as, for example, nitrogen or argon, and a pump assembly 12.

In operation, the probe 4 is immersed in the molten aluminum 18. The pump assembly 12 circulates a small volume of the carrier gas through the probe 4. Thus, as discussed in the publication "*ALSCAN: A New and Simple Technique for In-Line Analysis of Hydrogen in Aluminum Alloys*," by J. P. Martin et al. of Alcan International Limited of Quebec, Canada, which is hereby expressly incorporated herein by reference, the carrier gas is brought into contact with the molten aluminum 18 and recirculated until an equilibrium level is achieved between the hydrogen gas content in the carrier gas and the monoatomic hydrogen content in the molten aluminum 18. The analyzer 6 processes this data and provides a readout of the hydrogen concentration on the analyzer user interface 14.

It is generally recognized that, for a variety of reasons, differing hydrogen measurement results are obtained by different methods of measurement. For example, it has been discovered that, in measuring hydrogen concentration levels with, for example, the ALSCAN system, a bias or shift in hydrogen concentration rejection limits is required to compensate for variations in ambient conditions, such as, for example, seasonal variations in ambient humidity. Rejection limits represent the acceptable upper and lower hydrogen concentration range limitations for the particular molten aluminum alloy being tested. It has been discovered that, for example, when the ambient humidity level is low, the ALSCAN system measurements have rejection limits that are lower than when the ambient humidity level is high. In other words, the hydrogen level readouts provided on the analyzer user interface 14 vary depending on ambient humidity, thus requiring a bias or shift in the acceptable rejection limits. This adjustment or biasing of the rejection limits must be made on a substantially trial and error basis, resulting in uncertainty as to the accuracy and consistency of the measurement system 2 and the hydrogen concentration readings it provides. This problem has led to a constant search for a more efficient and accurate method and apparatus to measure hydrogen quantities in molten metals.

The NOTORP system is a relatively new measurement system using an electrochemical cell mounted inside a sampling tube or probe, which is immersed in molten aluminum. One side of the cell is exposed to the molten aluminum and the other side is in equilibrium with a carrier gas or reference gas such as, for example, argon. A solid state, proton conducting ceramic element is disposed within the immersion head of the sampling tube or probe. The electrochemical potential measured across the solid state, proton conducting ceramic element is processed by the analyzer, which in turn provides a digital readout on the user interface corresponding to the hydrogen concentration level in the molten metal. It has been discovered that NOTORP is substantially unaffected by factors such as ambient humidity. However, the NOTORP probe is complex and therefore costly to replace. Moreover, many aluminum casting shops and foundries are already using an existing measurement system such as an ALSCAN system. Replacement of the existing measurement system, with, for example, a new NOTORP system would be a costly and inefficient endeavor.

There is a need, therefore, for an improved method and apparatus for measuring gas concentrations levels in molten metals that avoids costly replacement of the measurement system currently being employed, and which is substantially unaffected by variations in ambient conditions, such as, for example, humidity.

SUMMARY OF THE INVENTION

As one embodiment of the invention, a method for measuring the concentration of gas in a liquid without requiring a bias to compensate for variations in ambient conditions, comprises the steps of: providing a measurement system including a probe connected to an analyzer with a housing enclosing a pump assembly, the pump assembly in fluid communication with the probe and the analyzer; providing a modification for the measurement system which substantially negates undesirable effects of ambient conditions on measurements taken by the measurement system; immersing the probe into the liquid, in order to take measurements of the concentration of gas in the liquid; and analyzing the measurements using the analyzer, the analyzer providing a gas concentration level readout.

The providing a modification step may further include the step of providing the pump assembly with at least one of, at least one gasket, at least one seal and at least one diaphragm; and wherein at least one of the at least one gasket, the at least one seal and the at least one diaphragm are made from a material compatible with the gas in the liquid and moisture and which is substantially unaffected by ambient humidity.

The providing a modification step may further include the step of providing a climate-controlled environment for at least a portion of the measurement system, in order to substantially eliminate the undesirable effects of ambient humidity on the measurement system. The step of providing a climate-controlled environment may include the steps of: surrounding the analyzer of the measurement system with a dry-air chamber; and filling the dry-air chamber with substantially dry air, or, the step of: filling the housing of the analyzer with dry air, in order that the pump assembly housed therein may operate in an environment substantially devoid of ambient humidity.

As another embodiment of the invention, a pump assembly, which is substantially unaffected by ambient humidity, if for use with a measurement system for measuring gas concentrations in a liquid, the measurement system including a probe connected to an analyzer the analyzer including a housing enclosing the pump assembly, the pump assembly in fluid communication with the probe and the analyzer. The pump assembly comprises: a motor; a pump housing for receiving the motor; a first member coupled to the pump housing and including a valve to controllably dispense a carrier gas to the probe; a second member coupled to the first member and including at least one orifice for receiving the carrier gas therethrough; a diaphragm disposed between the pump housing and the first member; at least one seal disposed in the valve of the first member; and at least one gasket disposed between the first member and the second member for controllably dispensing the carrier gas through the at least one orifice.

The at least one diaphragm, the at least one seal and the at least one gasket may be constructed of a material compatible with the gas in the liquid and with moisture and which is substantially unaffected by ambient humidity.

The pump assembly may further include a climate-controlled environment surrounding at least the pump assembly, in order to substantially eliminate undesirable effects of ambient humidity on the measurement system. The climate-controlled environment may include a dry-air chamber surrounding the analyzer and a dry-air supply for pumping dry air into the dry-air chamber, in order to substantially reduce the humidity within the dry-air chamber, or, a dry air supply for pumping dry air into the housing of the analyzer, thereby substantially reducing the humidity within the housing, in order that the pump assembly housed therein may operate in an environment substantially devoid of humidity.

As another embodiment of the invention, a measurement system is for measuring hydrogen gas concentrations in molten aluminum without requiring a bias to compensate for variations in ambient humidity. The measurement system, comprises: an analyzer including a housing; a probe coupled to the analyzer, the probe immersed in the molten aluminum, in order to take measurements of the hydrogen gas concentrations therein and to supply the measurements to the analyzer; and a pump assembly enclosed with the analyzer housing, the pump assembly comprising: a motor; a pump housing for receiving the motor; a first member coupled to the pump housing and including a valve to controllably dispense a carrier gas to the probe; a second member coupled to the first member and including at least one orifice for receiving the carrier gas therethrough; a diaphragm disposed between the pump housing and the first member; at least one seal disposed in the valve of the first member; and at least one gasket disposed between the first member and the second member for controllably dispensing the carrier gas through the at least one orifice.

The pump assembly may be structured to substantially eliminate undesirable effects caused by ambient humidity. At least one of the at least one diaphragm, the at least one seal and the at least one gasket of the pump assembly may be made from a material compatible with hydrogen and moisture.

The measurement system may further include a climate-controlled environment surrounding at least the pump assembly, in order to minimize the humidity within the climate-controlled environment. The climate-controlled environment may include a dry-air chamber surrounding the analyzer, the dry-air chamber being flushed with dry air supplied by a dry air supply, in order to substantially eliminate undesirable effects of ambient humidity on the analyzer, or, the housing of the analyzer and a dry air supply; and wherein dry air is pumped directly into the housing from the dry air supply, in order that the pump assembly may operate in an environment substantially devoid of humidity.

Accordingly, it is an object of the present invention to provide an "on-line" method of determining gas concentrations, such as, hydrogen concentrations, in molten metals, such as molten aluminum and its alloys, in order to substantially avoid defects in the resultant metal product that may be attributable to unacceptable gas concentrations.

It is a further object of this invention to provide such a method that provides accurate and reproducible gas concentration measurement results while being substantially unaffected by ambient humidity, temperature and dew point.

It is another object of the present invention to provide a method for accurately measuring hydrogen gas concentration in molten aluminum and its alloys without requiring a bias or adjustment in rejection limits to compensate for variations in ambient humidity levels.

It is yet another object of the present invention to provide such measurements by performing a low cost modification to existing gas measuring apparatus.

It is another object of the present invention to provide replacement parts, such as, for example, replacement seals, diaphragms and gaskets for the pump assemblies of existing gas measuring systems, in order to minimize the undesirable effects of ambient conditions, such as humidity, on measurements taken by the measuring system.

It is yet another object of this invention to provide a pump assembly and improved measuring system employing the aforementioned replacement components.

It is another object of this invention to provide a climate-controlled environment for at least the pump assembly of the measurement system, in order to substantially negate undesirable effects of ambient humidity on the measurement system.

These needs and others are satisfied by the present invention, which provides, among other things, a method and apparatus for measuring gas concentrations in molten metals without requiring an undesirable bias or adjustment in rejection limits, in order to compensate for ambient conditions, such as, humidity, dew point and temperature.

BRIEF DESCRIPTION OF THE DRAWINGS

A full understanding of the invention can be gained from the following description of the preferred embodiments when read in conjunction with the accompanying drawings in which.

DESCRIPTION OF THE PREFERRED EMBODIMENTS

For purposes of illustration, the present invention will be discussed in conjunction with the system for measuring hydrogen gas in molten aluminum and its alloys, which is commonly known in the art as ALSCAN, although it will become apparent that it could also be applied to other gas measurement systems expressly including, but not limited to TELEGAS, as well as to methods and apparatus for measuring gases other than hydrogen in substances other than molten metals.

As employed herein, the term "climate-controlled environment" refers to an environment in which factors such as, for example, ambient humidity and temperature may be readily controlled and regulated. For example, the exemplary dry-air chamber, discussed hereinbelow, creates a climate-controlled environment in which dry air may be pumped into the dry-air chamber to regulate the relative humidity level therein.

As employed herein, the term "dry air" refers to air with a low relative humidity level, such as, for example, a relative humidity level between about 1–4%. Relative humidity refers generally to the amount of moisture in the atmosphere and the temperature at which moisture condenses in the air is commonly referred to as the dew point.

As employed herein, the term "compatible material" refers to a material capable of harmoniously functioning or interacting with other predetermined materials, liquids or gases without experiencing undesirable or adverse effects or reactions therewith. For example, as discussed in detail hereinbelow, for the purposes of the present invention, a material that is compatible with moisture is one that substantially resists moisture penetration and thus, for example, undesirable measurement system effects associated therewith.

It has been discovered that the method and apparatus of the present invention permits measurement systems, such as, for example, ALSCAN systems, which are already owned and operated by aluminum casting shops and foundries, to provide accurate and reproducible hydrogen gas analysis without requiring expensive replacement of the entire existing system and without requiring undesirable biasing or adjustment of hydrogen concentration rejecting limits to compensate for variations in ambient conditions, such as humidity.

Figure 1:
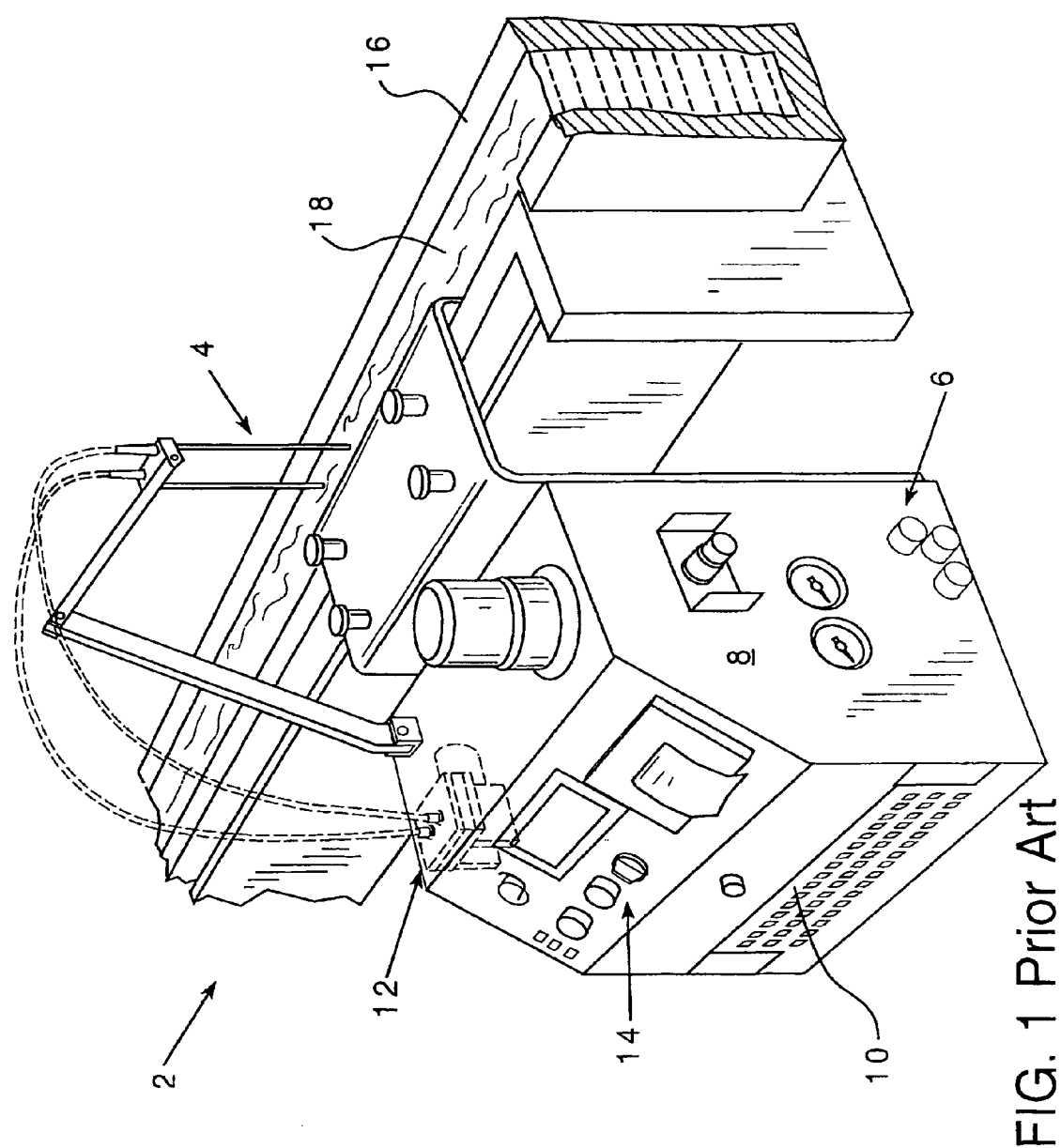
FIG. 1 is an isometric view of a measurement system for measuring gas concentrations in molten metals, with the pump assembly shown in phantom line drawing.
Figure 2:
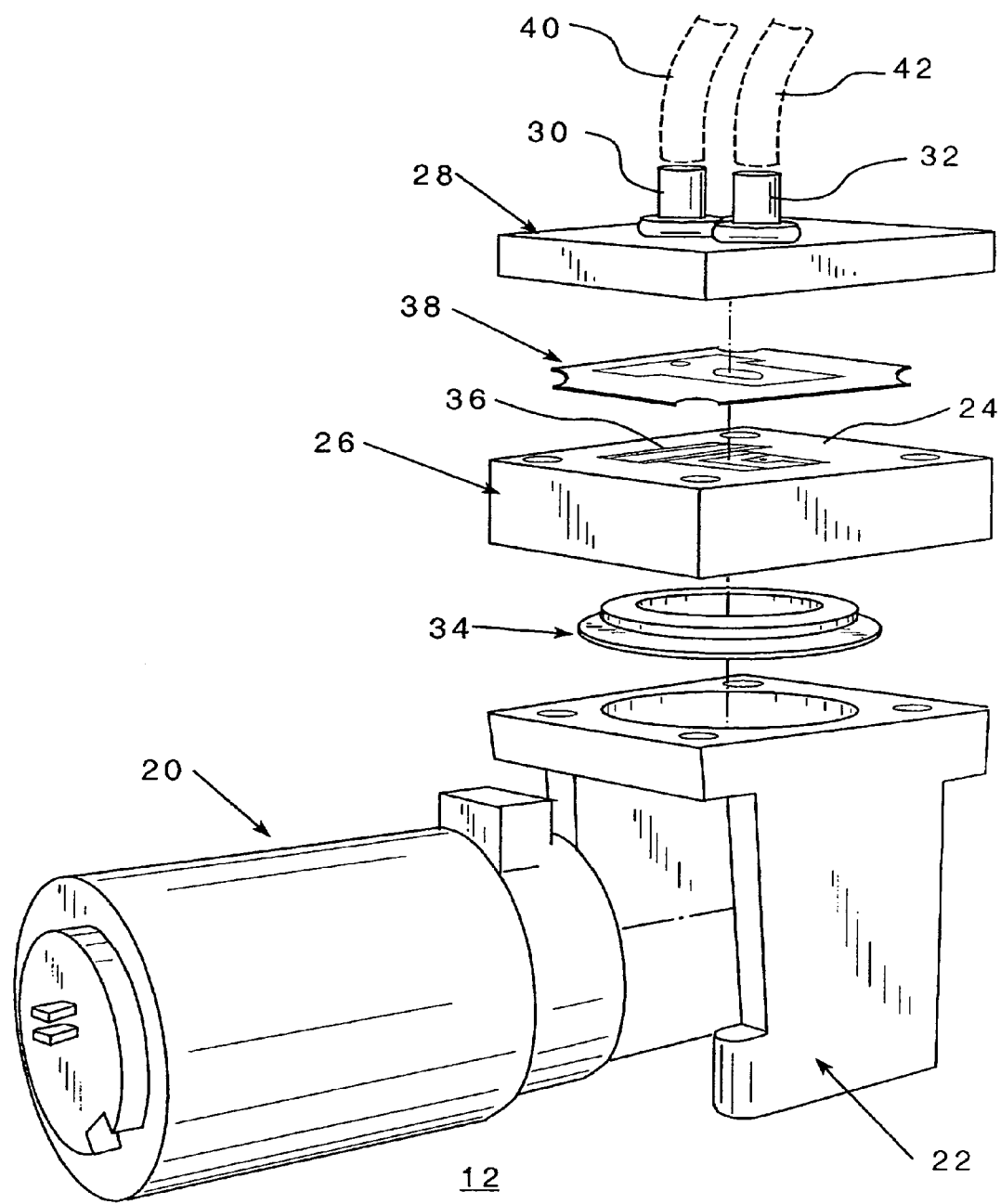
FIG. 2 is an exploded, isometric view of the pump assembly of FIG. 1, with probe lines shown in phantom line drawing.

FIG. 2 illustrates a method and apparatus for substantially eliminating adverse effects of ambient humidity on the measurement system 2, in accordance with the present invention, which includes providing a modified pump assembly 12, such as Model No. 800382-2 manufactured by Sensidyne Incorporated of 16333 Bay Vista Drive, Clearwater, Fla. 33760. As shown, the pump assembly 12 includes a motor 20 for circulating the carrier gas supplied by the gas reservoir 10 (FIG. 1), within the probe 4 (FIG. 1). The motor 20 is attached to a pump housing 22. A first member 24 having a valve 26 is disposed on top of the pump housing 22. A diaphragm 34 is disposed between the pump housing 22 and the first member 24, as shown. The valve 26 of the first member 24 includes at least one seal 36 (one seal 36 is shown in FIG. 2). The valve 26 and the seal 36 therein facilitate the controlled dispensing of the carrier gas to the probe 4 (FIG. 1). A second member 28 is disposed on top of the first member 24. The second member includes at least one orifice 30, 32 (two are shown in FIG. 2), for circulating the carrier gas therethrough to probe lines 40, 42, which connect the probe 4 (FIG. 1) to the orifice 30, 32 of the pump assembly 12. A gasket 38 is disposed between the first and second members 24, 28, as shown. The gasket 38 further facilitates controlled circulation of the carrier gas within the probe 4 via the orifice 30, 32 of the second member 28.

The diaphragm 34, seal 36 and gasket 38 (best shown in FIGS. 3–5) of the pump assembly 12 are typically made from an elastomer such as, for example, silicone, neoprene, or EPDM. Each of these elastomers reacts differently to hydrogen gas and other byproducts produced during the manufacture of aluminum, such as, for example, chlorine gas, alloying elements and impurities. It has been discovered through the present invention that modifying the pump assembly 12 by replacing these elastomeric pump assembly components with components made from a material that is compatible with hydrogen gas and substantially unaffected by, or impermeable to, moisture, such as, for example, the material commonly associated with the trade designation VITON, a fluoroelastomer produced by DuPont Dow Elastomers of Wilmington, Del. Such material effectively improves the accuracy and reliability of hydrogen gas concentration measurements taken by the measurement system 2 (FIG. 1). It has further been discovered that the aforementioned pump assembly 12 and method of modification thereof, of the present invention, substantially eliminates undesirable effects of ambient moisture on the measurement system 2 (FIG. 1).

Figure 3:
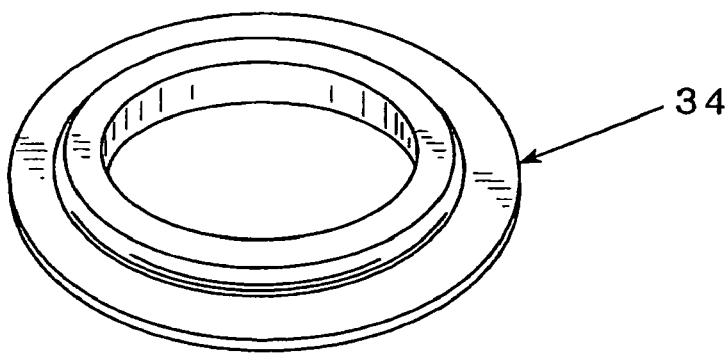
FIG. 3 is an isometric view of a diaphragm for the pump assembly of FIG. 2, in accordance with the present invention.
Figure 4:
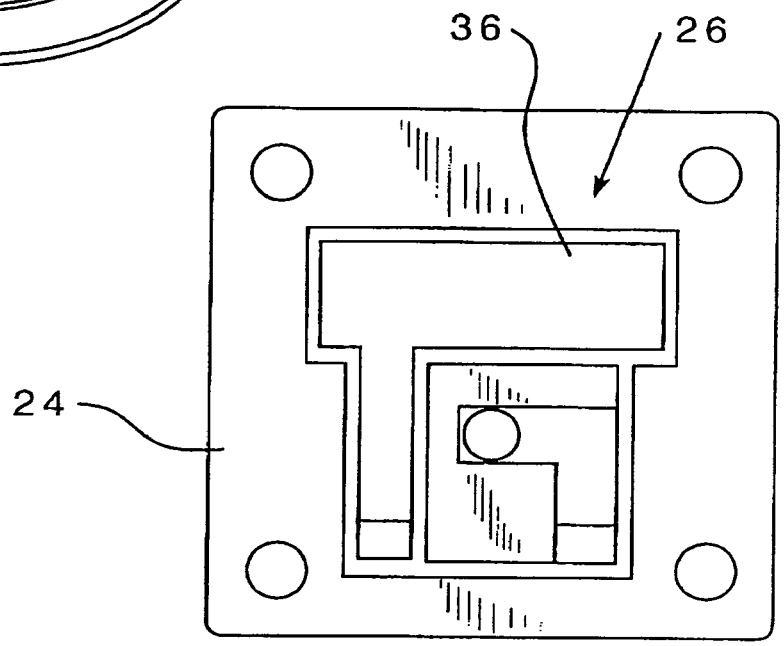
FIG. 4 is a vertical elevational view of the valve with a seal, for the pump assembly of FIG. 2, in accordance with the present invention.
Figure 5:
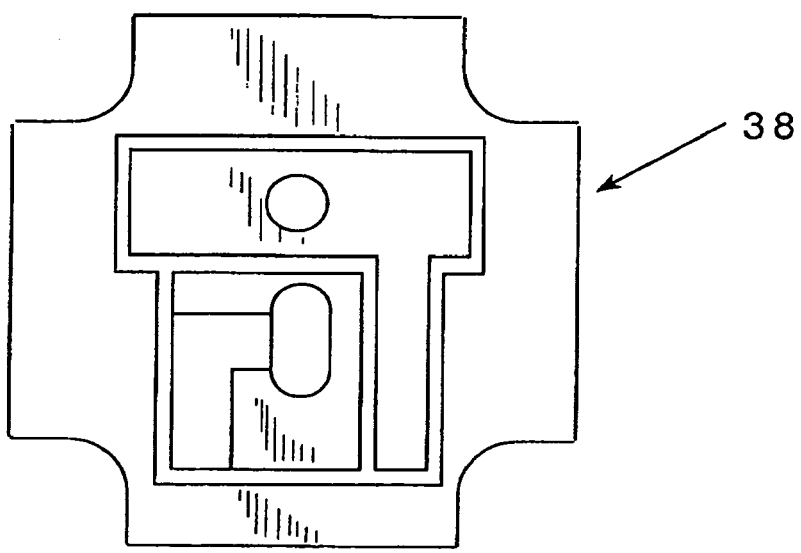
FIG. 5 is a vertical elevational view of a gasket for the pump assembly of FIG. 2, in accordance with the present invention.

FIGS. 3–5 show the pump assembly components, which are replaced with a hydrogen and moisture compatible material, such as VITON, in accordance with the present invention. VITON fluoroelastomers are well suited for general molded goods such as O-rings, seals, gaskets, diaphragms and other simple and complex shapes. Of particular interest, VITON exhibits good compatibility with both moisture and hydrogen gas as is substantially impermeable to either. Table 1 lists the material properties of VITON. Table 1 has been reproduced from "The Rubber Engineering Guide," found at the internet web address http://www-.molders.com/rubber_engineering_guide.html, which is hereby expressly incorporated by reference herein.

TABLE 1

Characteristics of Rubber Compounds
Rubber Engineering Guide
(http://www.molders.com/rubber_engineering_guide.html)

| | Viton (FKM) |
|---|---|
| Specific gravity | 1.85 |
| Tensile strength | 2500 |
| Elongation, max | 3x |
| Hardness, Shore A | 60–95 |
| Brittle point (F) | −40 |
| Permeation rate for water under vacuum. | 4.00E−07 sq-cm/sec |

It has been discovered through the present invention that the superior material properties of VITON, as compared to known prior art sealing elastomers, provide substantially improved measurement system 2 (FIG. 1) performance and accuracy, when employed in the pumping assemblies 12 (FIG. 2) thereof.

FIG. 3 shows the exemplary diaphragm 34, which as shown in FIG. 2, is disposed between the pump housing 22 and the first member 24 of the pump assembly 12. The diaphragm 34, as shown, is substantially circular in shape, forming a ring with a rib-shaped protrusion. The diaphragm 34 sealingly engages both the pump housing 22 and the first member 24 of the pump assembly 12. It has been discovered by the present invention that replacing the existing diaphragm with one made from a material more compatible with hydrogen and moisture, such as, for example, VITON, substantially negates the adverse effects of ambient humidity on the measurement system 2 (FIG. 1).

FIG. 4 illustrates the exemplary first member 24 of the pump assembly 12 (FIG. 1), which includes a valve 26 employing a reed valve elastomer seal 36 made from a hydrogen and moisture compatible material, such as VITON. As shown, the seal 36 generally comprises a thin band extending across a recess in the valve 26, in order to facilitate controlled disbursement of the carrier gas therethrough as required by the pump motor 20 (FIG. 1). It has been discovered by the present invention that the exemplary VITON seal 36 helps to substantially negate the adverse effects of ambient humidity on the measurement system 2 (FIG. 1).

FIG. 5 illustrates the exemplary gasket 38, made from a hydrogen and moisture compatible material, such as VITON, disposed between the first and second members 24, 28 of the pump assembly 12 (FIG. 2). As shown, the gasket is molded to correspond with and to engage the valve 26 (FIG. 4) of the first member 24 (FIG. 4), in order to provide a substantially impermeable seal between the first and second members 24, 28 (best shown in FIG. 2). The gasket 38 also includes openings corresponding to the orifice 30, 32 of the second member 28 (best shown in FIG. 2), in order to permit circulation of the carrier gas to and from the pump assembly 12 through the valve 26 and orifice 30, 32, respectively. As it has been discovered by the present invention that the exemplary VITON gasket 38 helps to substantially negate the adverse effects of ambient humidity on the measurement system 2 (FIG. 1).

It will be appreciated that the pump assembly 12 and method of modification thereof, of the present invention, may include any combination of gaskets 38, seals 36 and diaphragms 34 made from any suitable material, in addition to the exemplary VITON material, which substantially negates the adverse effects of ambient conditions, such as, humidity, on the measurement system 2 (FIG. 1).

Figure 6:
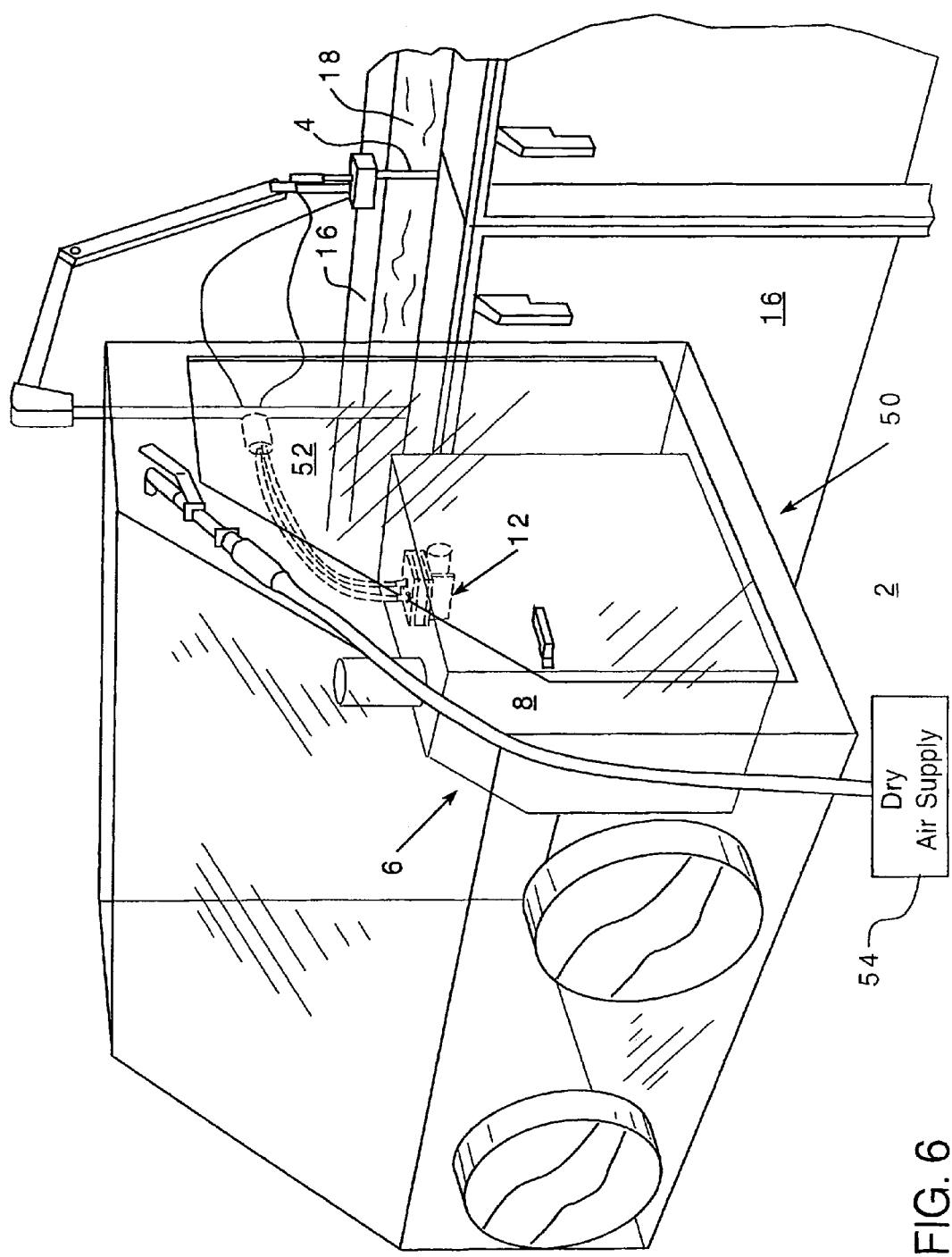
FIG. 6 is an isometric view of an assembly for measuring gas concentration levels in molten metals, in accordance with an embodiment of the present invention, with the pump assembly shown in phantom line drawing.

FIG. 6 illustrates a method and apparatus for substantially eliminating adverse effects of ambient humidity, in accordance with the present invention, including a climate-controlled environment 50 for at least the pump assembly 12 of the measurement system 2. As shown, the exemplary climate-controlled environment 50 includes a dry-air chamber 52, which is constructed of any known or suitable material, such as, for example, PLEXIGLAS or LEXAN, and which surrounds the analyzer 6. Dry air is then be pumped into the dry-air chamber 52 from a dry air supply 54, in order to dry the air therein. The dry air reduces the relative humidity to a predetermined desired level, thereby substantially eliminating undesirable effects associated therewith, such as, for example, shifts in hydrogen gas concentration measurement readings, requiring a shift in the acceptable hydrogen gas rejection limits.

It has been discovered by the present invention that surrounding the analyzer 6 of the measurement system 2 and the pump assembly 12 enclosed within the housing 8 thereof, with dry air, such as, for example, air with a relative humidity level of between about 1–4%, substantially improves the accuracy and reproducibility of hydrogen gas concentration measurement readings taken using the existing measurement system 2.

It will be appreciated that the climate-controlled environment 50 could alternatively include pumping dry air from the dry air supply 54 directly into the housing 8 of the analyzer 6, rather than employing the exemplary dry-air chamber 52. In such an embodiment, which, for simplicity of illustration has not been shown, the analyzer housing 8 would function as a self-contained dry-air chamber, wherein the pump assembly 12 housed therein is surrounded with dry air having a low relative humidity level, such as, for example, between about 1–4% humidity. The housing 8 of the analyzer 6 would thereby function as a climate-controlled environment similarly to the dry-air chamber 52 of FIG. 6. It will also be appreciated that the climate-controlled environment 50 and method of use thereof, of the present invention, may be employed individually or in combination with the aforementioned measurement system 2, pump assembly 12 and method of modification thereof, of the present invention, in order to minimize undesirable effects of variations in ambient conditions, such as, for example, humidity on the measurement system 2 and method of use thereof.

Figure 7:
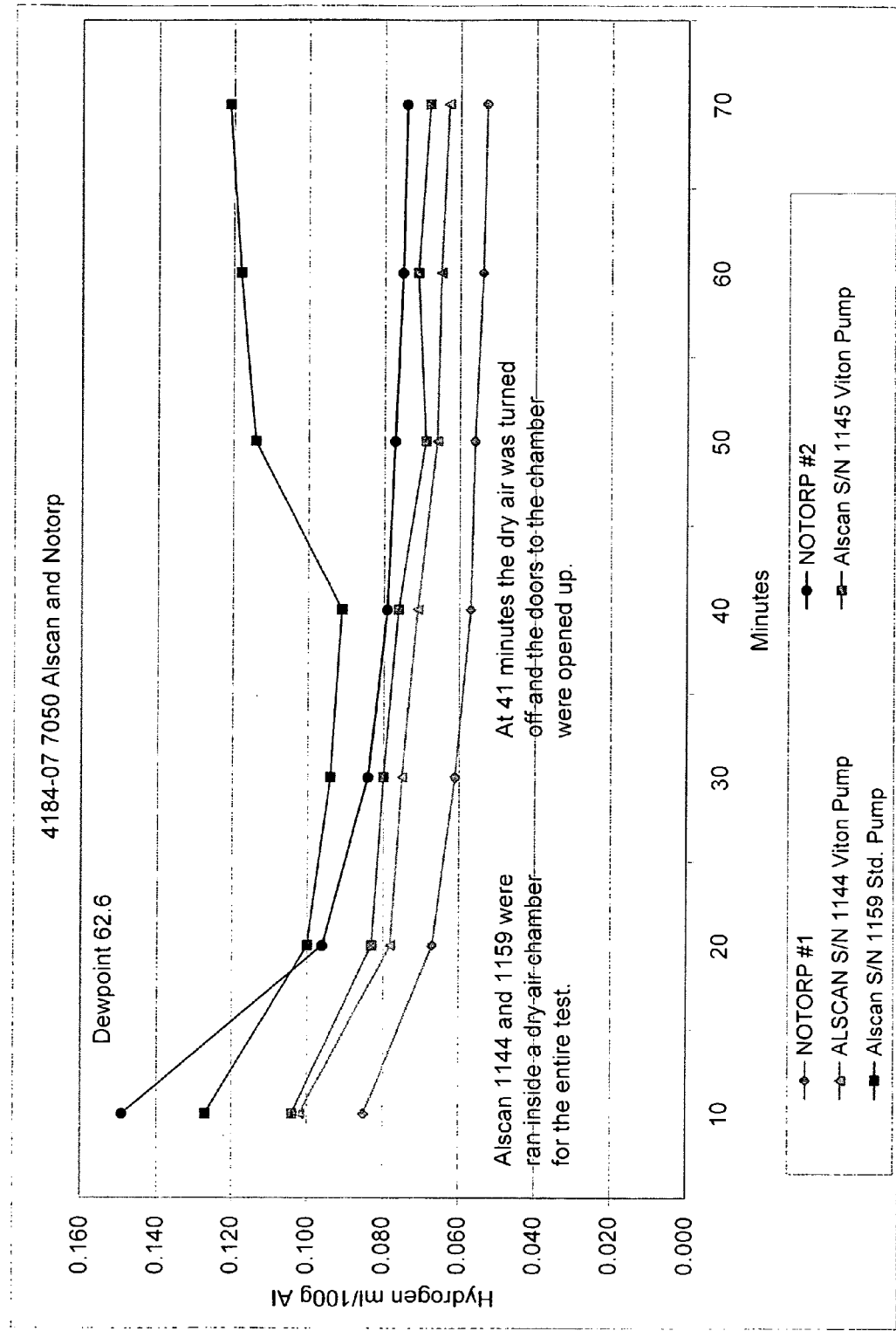
FIG. 7 is a graph comparing the measurements of hydrogen gas concentration measurements in molten aluminum alloy 7050, taken using the method and apparatus of the present invention, as compared to other known methods and apparatus, where the ambient dew point was 62.6° F.
Figure 8:
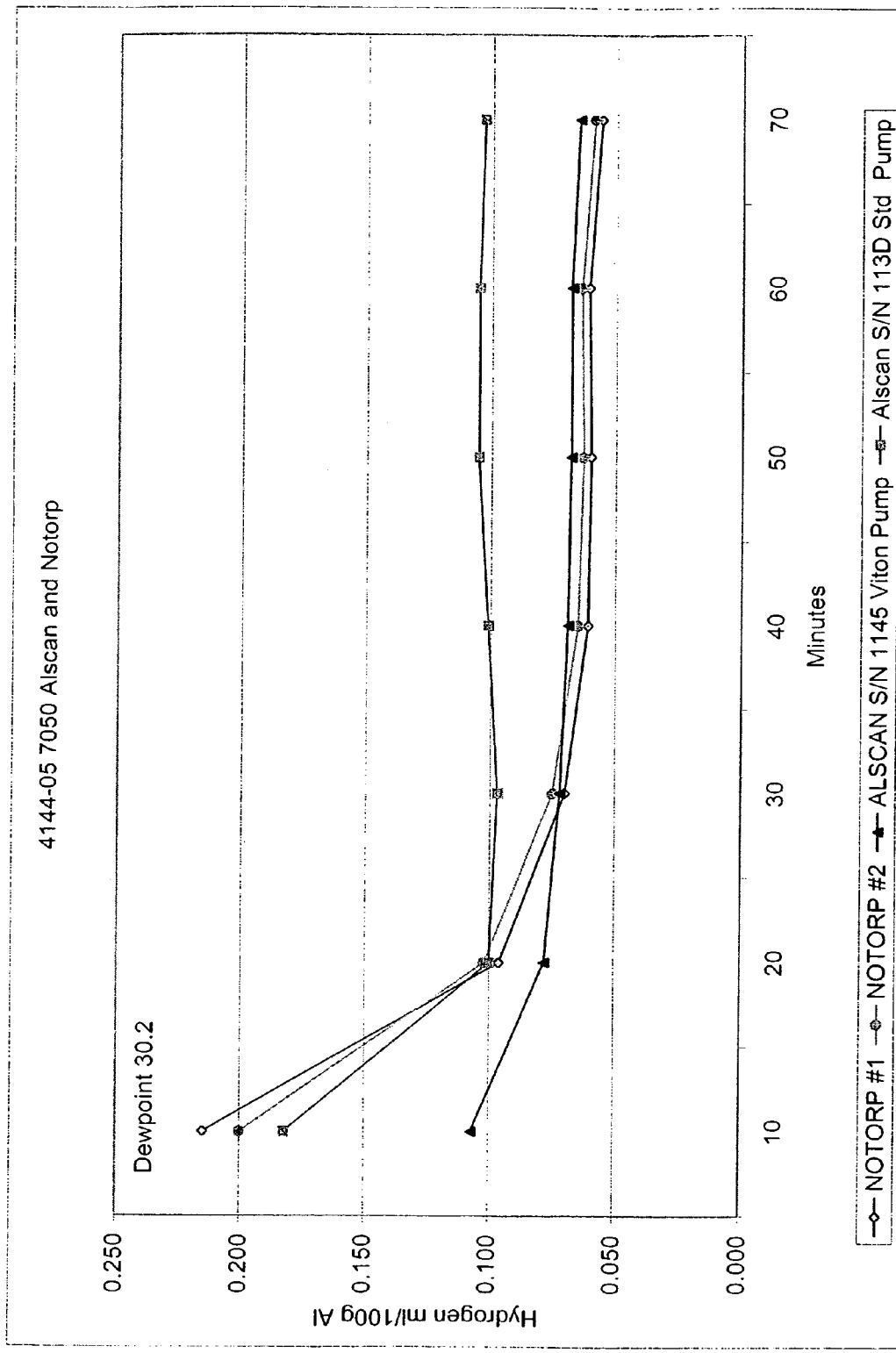
FIG. 8 is a graph comparing the measurements of hydrogen gas concentration measurements in molten aluminum alloy 7050, taken using the method and apparatus of the present invention, as compared to other known methods and apparatus, where the ambient dew point was 30.2° F.
Figure 9:
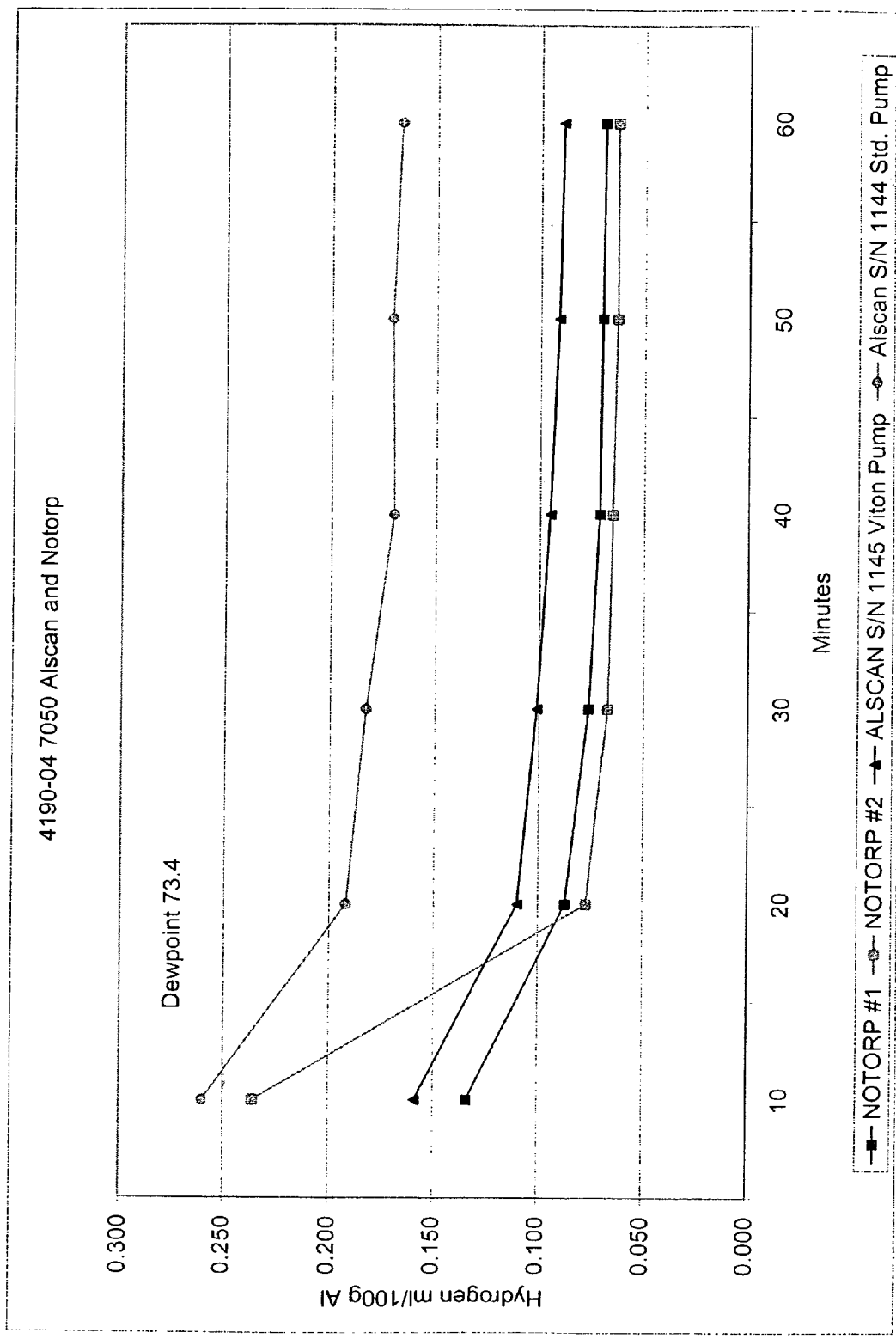
FIG. 9 is a graph comparing the measurements of hydrogen gas concentration measurements in molten aluminum alloy 7050, taken using the method and apparatus of the present invention, as compared to other known methods and apparatus, where the ambient dew point was 73.4° F.

FIGS. 7–9 will be discussed in relation to the following examples, through which the advantageous discoveries of the present invention will become even more apparent. The examples are given for purposes of illustration only and are in no way limiting.

EXAMPLE 1

The following experiment was conducted in order to compare hydrogen gas concentration measurements taken using the method and apparatus of the present invention, as compared to four other hydrogen concentration measurement systems. The molten aluminum alloy tested was AA7050. The dew point during the test was 62.6° F. The ambient temperature was 92° F. and the relative humidity was 38%. The five measurement systems included two NOTORP systems designated NOTORP #1 and NOTORP #2, respectively (FIG. 7), and three ALSCAN systems, respectively, designated by the serial numbers 1144, 1145, and 1159 (FIG. 7). Two of the ALSCAN systems 1144 and 1145 employed the modified pump assembly 12 (best shown in FIG. 2) of the present invention.

A dry-air chamber 52, as shown in FIG. 6, was employed to house ALSCAN systems 1144 and 1159, in order to create climate-controlled environment 50 with controllable ambient conditions, such as, for example, humidity. For comparison purposes, the remaining three measurement systems, NOTORP #1, NOTORP #2 and ALSCAN 1145, were all located outside of the dry air chamber 52.

Before the experiment was conducted, the dry air chamber 52 was flushed with dry air having a relative humidity of approximately 1–2%. Hydrogen gas concentration measurements were then recorded by all five measurement systems, simultaneously, over a period of 70 minutes. Table 1 lists the hydrogen measurements taken by each measurement system during the test. The columns associated with ALSCAN 1144 and 1145, are bolded to highlight or differentiate the measurements recorded by the measurement systems employed in accordance with the method and apparatus of the present invention.

TABLE 1

| Time min. | Notorp 1 H ml/ 100 g Al | Notorp 2 H ml/ 100 g Al | Alscan 1144 H ml/ 100 g Al | Alscan 1145 H ml/ 100 g Al | Alscan 1159 H ml/ 100 g Al |
|---|---|---|---|---|---|
| 10 | 0.085 | 0.149 | 0.102 | 0.104 | 0.127 |
| 20 | 0.067 | 0.096 | 0.078 | 0.083 | 0.1 |
| 30 | 0.061 | 0.084 | 0.075 | 0.08 | 0.094 |
| 40 | 0.057 | 0.079 | 0.071 | 0.076 | 0.091 |
| 50 | 0.056 | 0.077 | 0.066 | 0.069 | 0.114 |
| 60 | 0.054 | 0.075 | 0.065 | 0.071 | 0.118 |
| 70 | 0.053 | 0.074 | 0.063 | 0.068 | 0.121 |

At approximately 41 minutes into the test, in order to test the effects of a variation in ambient humidity on the measurement systems, the dry air was turned off and the dry air chamber 52 was opened up. As shown in Table 1 and the corresponding graph shown in FIG. 7, the modified ALSCAN system 1144 located inside the dry air chamber 52 was unaffected by the rapid increase in humidity. Furthermore, the modified ALSCAN system 1145, which was disposed outside the dry air chamber 52 throughout the entire test, was likewise unaffected by the ambient humidity. In fact, it provided readings substantially similar to modified ALSCAN system 1144, which was located inside the dry-air chamber 52 throughout the test. This clearly shows that ALSCAN systems in accordance with the method and apparatus of the present invention are substantially unaffected by variations in ambient humidity. This discovery is further substantiated by the fact that, the ALSCAN system 1159, with the unmodified or standard pump assembly 12, was in fact affected by the influx of humidity. As shown, the unmodified ALSCAN system 1159, when subjected to the increase in humidity, began providing measurement readings much higher than the other four systems.

The NOTORP systems were included primarily for comparison purposes, because it is commonly known in the art that NOTORP appears to be unaffected by ambient humidity. FIG. 7 substantiates this fact and also shows the improvement in ALSCAN measurements when employing the method and apparatus of the present invention. The experiment, as depicted in Table 1 and FIG. 7, clearly demonstrates that the method and apparatus of measuring hydrogen concentration levels, of the present invention yields accurate and consistent hydrogen concentration measurements substantially comparable to those generated by, for example, NOTORP. The experiment also substantiates the improvement in performance of an ALSCAN system modified in accordance with the present invention, as compared to a stock or unmodified measurement system. Furthermore, the experiment substantiates the discovery of the present invention, that a pump assembly modified with a hydrogen and moisture compatible material, such as VITON, is substantially unaffected by ambient humidity and variations thereof.

To further substantiate the improved measurement method and apparatus of the present invention, the following two additional experiments were conducted under different ambient conditions.

EXAMPLE 2

The following experiment was conducted under ambient conditions different than those of EXAMPLE 1. The ambient temperature during the experiment was 69° F., and the relative humidity was 32%. The dew point was 30.2° F. For consistency, the same molten aluminum alloy was tested, AA7050, and hydrogen gas concentration measurements were again, simultaneously taken over a period of 70 minutes.

Unlike EXAMPLE 1, however, four, rather than five, measurement systems were used during this experiment. Furthermore, no climate-controlled environment 50, such as the dry-air chamber 52, shown in FIG. 6, was employed. accordingly, all four measurement systems, NOTORP 1, NOTORP 2, ALSCAN 1145 and ASLSCAN 113D were all exposed to ambient conditions, such as, for example, humidity throughout the entire duration of the experiment. The pump assembly 12 of ALSCAN 1145 was modified, in accordance with the present invention, to include a diaphragm 34, seal 36 and gasket 38 (best shown in FIGS. 2–5), made of a material, such as VITON, which is compatible with hydrogen and moisture. The pump assembly 12 of ALSCAN 113D was not modified.

Table 2 lists the hydrogen concentration measurements recorded by each of four measurement systems over the 70 minute testing period. The column ALSCAN 1145 is bolded to highlight or differentiate the measurements recorded in accordance with the method and apparatus of the present invention.

TABLE 2

| Time min. | Notorp 1 H ml/100 g Al | Notorp 2 H ml/100 g Al | Alscan 1145 H ml/100 g Al | Alscan 113D H ml/100 g Al |
|---|---|---|---|---|
| 10 | 0.215 | 0.2 | 0.107 | 0.182 |
| 20 | 0.096 | 0.102 | 0.078 | 0.1 |
| 30 | 0.07 | 0.075 | 0.072 | 0.097 |
| 40 | 0.061 | 0.065 | 0.069 | 0.101 |
| 50 | 0.06 | 0.063 | 0.068 | 0.105 |
| 60 | 0.061 | 0.064 | 0.068 | 0.105 |
| 70 | 0.056 | 0.059 | 0.065 | 0.103 |

As shown in Table 2 and the corresponding graph of FIG. 8, following an initial calibration time period of approximately 30 minutes, the ALSCAN system 1145 with the modified pump assembly 12, as in EXAMPLE 1, performed substantially on par with the NOTORP systems. This experiment further substantiates the fact that the method and apparatus discovered through the present invention substantially eliminates undesirable effects caused by variations in ambient conditions, such as, humidity, on the measurement system 2. For example, as shown in FIG. 8, the unmodified ALSCAN system 113D, as in EXAMPLE 1, returned hydrogen concentration readings higher than the other three measurement systems, NOTORP 1, NOTORP 2, and the modified ALSCAN system 1145, thus illustrating undesirable effects of humidity on standard measurement systems and the ability to eliminate such adverse effects through the method and apparatus discovered by the present invention.

Accordingly, the discoveries of the present invention permit a measurement system currently being used by an aluminum casting shop or foundry, to be quickly and easily modified, at low cost, to operate accurately and on par with complex and expensive replacement measurement systems.

EXAMPLE 3

The following experiment was conducted under ambient conditions, which were different than EXAMPLE 1 and EXAMPLE 2. The ambient temperature during the experiment was 92° F., and the relative humidity was 55%. The dew point was 73.4° F. The same molten aluminum alloy was tested, AA7050. Hydrogen gas concentration measurements for this experiment, however, were taken over a period of 60 minutes, rather than the 70 minute duration as in EXAMPLES 1 and 2.

As in EXAMPLE 2, four, rather than five, measurement systems were used during the experiment and no climate-controlled environment 50, such as the dry-air chamber 52 shown in FIG. 6, was employed. Accordingly, all four measurement systems, NOTORP 1, NOTORP 2, ALSCAN 1145, and ALSCAN 1144 were all exposed to ambient conditions throughout the entire experiment.

The pump assembly 12 of ALSCAN 1145 was modified in accordance with the present invention, as in EXAMPLE 2, to include a diaphragm 34, seal 36 and gasket 38 (best shown in FIGS. 2–5) made from a material, such as VITON which is compatible with hydrogen and moisture, while ALSCAN 1144 had a standard or unmodified pump assembly 12. Table 3 lists the hydrogen concentration readings recorded by each of the measurement systems over the 60 minute testing period. The column associated with ALSCAN 1145 is bolded to highlight or differentiate the measurements recorded in accordance with the method and apparatus of the present invention.

TABLE 3

| Time min. | Notorp 1 H ml/100 g Al | Notorp 2 H ml/100 g Al | Alscan 1145 H ml/100 g Al | Alscan 1144 H ml/100 g Al |
|---|---|---|---|---|
| 10 | 0.134 | 0.236 | 0.159 | 0.26 |
| 20 | 0.087 | 0.077 | 0.11 | 0.192 |
| 30 | 0.076 | 0.067 | 0.101 | 0.183 |
| 40 | 0.071 | 0.065 | 0.095 | 0.17 |
| 50 | 0.07 | 0.063 | 0.091 | 0.171 |
| 60 | 0.069 | 0.063 | 0.089 | 0.167 |

As shown, in Table 3 and the corresponding graph of FIG. 9, the modified ALSCAN system 1145, again, as in EXAMPLES 1 and 2, performed substantially on par with the NOTORP systems. Specifically, ALSCAN system 1145 was modified in accordance with the method and apparatus of the present invention, to employ a pump assembly 12 with pump components, made of a material, such as VITON, which is compatible with hydrogen and moisture. The modified ALSCAN system 1145 was substantially unaffected by ambient humidity. However, the unmodified ALSCAN system 1144 returned hydrogen concentration readings higher than the other three measurement systems, NOTORP 1, NOTORP 2, and the modified ALSCAN system 1145.

Accordingly, this experiment further substantiates the discovery that existing measurement systems, such as, for example, ALSCAN systems currently being used by aluminum casting shops and foundries, are in fact undesirably affected by ambient conditions, thereby requiring an undesirable bias or adjustment in hydrogen concentration rejection limits, to compensate for such effects, and therefore leading to uncertainty as to the accuracy of the measurement readings provided by the system.

For example, as shown in FIGS. 7–9, the variations in ambient humidity, dew point and temperature between the three experiments of EXAMPLES 1–3 resulted in hydrogen concentration measurement variations for the unmodified ALSCAN systems 1159 (EXAMPLE 1), 113D (EXAMPLE 2) and 1144 (EXAMPLE 3). However, none of the measurement systems employed in accordance with the method and apparatus of the present invention, namely, ALSCAN systems 1144 (EXAMPLE 1) and 1145 (EXAMPLE 1, EXAMPLE 2 and EXAMPLE 3), were undesirably affected by the variations in dew point, humidity and temperature.

Accordingly, the present invention provides an effective, low cost method and apparatus for substantially eliminating undesirable effects on the measurement of hydrogen gas in molten metals, believed to be caused by variations in ambient conditions such as humidity, dew point and temperature. Thus, the need to bias or adjust hydrogen concentration rejection limits to compensate for variations in such conditions is substantially eliminated, thereby improving the consistency, accuracy and reliability of existing measurement systems without requiring costly replacement of the entire system.

While specific embodiments of the invention have been described in detail, it will be appreciated by those skilled in the art that various modifications and alternatives to those details, in addition to those discussed above, could be developed in light of the overall teachings of the disclosure. Accordingly, the particular arrangements disclosed are meant to be illustrative only, and not limiting as to the scope of the invention which is to be given the full breadth of the claims appended and any and all equivalents thereof.

What is claimed is:

1. A pump assembly, which is substantially unaffected by ambient humidity, for use with a measurement system for measuring gas concentrations in a liquid, said measurement system including a probe connected to an analyzer said analyzer including a housing enclosing said pump assembly, said pump assembly in fluid communication with said probe and said analyzer, said pump assembly comprising: a motor; a pump housing for receiving said motor; a first member coupled to said pump housing and including a valve to controllably dispense a carrier gas to said probe; a second member coupled to said first member and including at least one orifice for receiving said carrier gas therethrough; a diaphragm disposed between said pump housing and said first member; at least one seal disposed in the valve of said first member; and at least one gasket disposed between said first member and said second member for controllably dispensing said carrier gas through said at least one orifice.

2. The pump assembly of claim 1 wherein at least one of said at least one diaphragm, said at least one seal and said at least one gasket are constructed of a material compatible with said gas in said liquid and with moisture.

3. The pump assembly of claim 2 wherein said liquid is molten aluminum; and wherein said gas in said liquid is hydrogen.

4. The pump assembly of claim 2 wherein said material compatible with said gas in said liquid and with moisture is a fluoroelastomer.

5. The pump assembly of claim 4 wherein all of said at least one diaphragm, said at least one seal and said at least one gasket are constructed from said fluoroelastomer.

6. The pump assembly of claim 1 wherein at least one of said at least one gasket, said at least one seal and said at least one diaphragm are substantially unaffected by ambient humidity.

7. The pump assembly of claim 1 further including a climate-controlled environment surrounding at least said pump assembly, in order to substantially eliminate undesirable effects of ambient humidity on said measurement system.

8. The pump assembly of claim 7, wherein said climate-controlled environment includes a dry-air chamber surrounding said analyzer and a dry-air supply for pumping dry air into said dry-air chamber, in order to substantially reduce the humidity within said dry-air chamber.

9. The pump assembly of claim 7, wherein said climate-controlled environment includes a dry air supply for pumping dry air into said housing of said analyzer, thereby substantially reducing the humidity within said housing, in order that said pump assembly housed therein may operate in an environment substantially devoid of humidity.

10. A measurement system for measuring hydrogen gas concentrations in molten aluminum without requiring a bias to compensate for variations in ambient humidity, said measurement system, comprising: an analyzer including a housing; a probe coupled to said analyzer, said probe immersed in said molten aluminum, in order to take measurements of said hydrogen gas concentrations therein and to supply said measurements to said analyzer; and a pump assembly enclosed with said analyzer housing, said pump assembly comprising: a motor; a pump housing for receiving said motor; a first member coupled to said pump housing and including a valve to controllably dispense a carrier gas to said probe; a second member coupled to said first member and including at least one orifice for receiving said carrier gas therethrough; a diaphragm disposed between said pump housing and said first member; at least one seal disposed in the valve of said first member; and at least one gasket disposed between said first member and said second member for controllably dispensing said carrier gas through said at least one orifice.

11. The measurement system of claim 10 wherein said pump assembly is structured to substantially eliminate undesirable effects caused by ambient humidity.

12. The measurement system of claim 11 wherein at least one of said at least one diaphragm, said at least one seal and said at least one gasket of said pump assembly is made from a material compatible with hydrogen and with moisture.

13. The pump assembly of claim 12 wherein said material compatible with hydrogen and with moisture is a fluoroelastomer.

14. The pump assembly of claim 13 wherein all of said at least one diaphragm, said at least one seat and said at least one gasket are constructed from said flouroelastomer.

15. The measurement system of claim 10 further including a climate-controlled environment surrounding at least said pump assembly, in order to minimize the humidity within said climate-controlled environment.

16. The measurement system of claim 15 wherein said climate-controlled environment includes a dry-air chamber surrounding said analyzer, said dry-air chamber being flushed with dry air supplied by a dry air supply, in order to substantially eliminate undesirable effects of ambient humidity on said analyzer.

17. The measurement system of claim 15 wherein said climate-controlled environment includes said housing of said analyzer and a dry air supply; and wherein dry air is pumped directly into said housing from said dry air supply, in order that said pump assembly may operate in an environment substantially devoid of humidity.

* * * * *